United States Patent [19]
Ogawa et al.

[11] Patent Number: 5,324,543
[45] Date of Patent: Jun. 28, 1994

[54] METHOD OF MANUFACTURING AN ADSORBED MONOMOLECULAR FILM

[75] Inventors: Kazufumi Ogawa, Hirakata; Tadashi Ootake, Neyagawa; Mamoru Soga, Osaka, all of Japan

[73] Assignee: Matsushita Electric Industrial Co., Ltd., Osaka, Japan

[21] Appl. No.: 20,534

[22] Filed: Feb. 22, 1993

Related U.S. Application Data

[62] Division of Ser. No. 804,668, Dec. 10, 1991, Pat. No. 5,225,274.

[30] Foreign Application Priority Data

Dec. 10, 1990 [JP] Japan .................. 2-400981

[51] Int. Cl.$^5$ .............................. B05D 5/08
[52] U.S. Cl. ................... 427/387; 427/407.1; 427/419.7
[58] Field of Search ............ 427/407.1, 419.7, 387

[56] References Cited

U.S. PATENT DOCUMENTS 5,010,356  4/1991  Albinson ................ 427/387
5,143,750  9/1992  Yamagata et al. ......... 427/57

FOREIGN PATENT DOCUMENTS 0491251  6/1992  European Pat. Off. .
0497189  8/1992  European Pat. Off. .

OTHER PUBLICATIONS

Abstract of JP 04-132637, May, 1992.
Abstract of JP 04-331785, Nov. 1992.
Abstract of JP 04-255307, Sep. 1992.

Primary Examiner—Terry J. Owens
Assistant Examiner—Erma Cameron
Attorney, Agent, or Firm—Fish & Richardson

[57] ABSTRACT

The invention provides a method of forming a monomolecular film of fluorine-containing molecules on a substrate surface such that the film has a uniform thickness with minimal surface irregularities and is substantially pin hole free. The invention also provides for a substrate obtained by using the same method which has excellent water- and oil-repelling, anti-fogging, and anti-contaminating properties. The monomolecular film is formed on the substrate surface either directly or via a given protective film. The monomolecular film coating is characterized by a plurality of different chlorosilane-based surface active materials which are different in molecular length and have a fluorine group. The surface irregularities of the film are generally confined to the molecular level.

5 Claims, 2 Drawing Sheets

METHOD OF MANUFACTURING AN ADSORBED MONOMOLECULAR FILM

This application is a division of U.S. application Ser. No. 07/804,668, filed Dec. 10, 1991, now U.S. Pat. No. 5,225,274.

FIELD OF THE INVENTION

This invention relates to functional monomolecular films and, more particularly, to water-repellent, oil-repellent, anti-fogging and/or anti-contaminating films. More particularly, this invention relates to materials such as metals, ceramics, plastics, glass, etc. having a fluorine film coating.

BACKGROUND OF THE INVENTION

Heretofore, for improving the water- and oil-repelling properties of substrate surfaces, it has been a known practice to coat silicon-based surface active agents onto substrate surfaces or fluorocarbon-based polymer suspensions onto substrate surfaces.

Generally, a material with a fluorine resin coating is obtained by making the surface coarse by means of electrolytic etching or surface roughening to increase adhesion with a fluorine-based polymer. The surface is coated with a fluorine-based polymer suspension, followed by baking.

The prior art substrate is generally known to exhibit improved water- and oil-repelling properties and can be readily manufactured. However, if the film coating on the substrate surface is insufficiently thin, it results in generation of pin holes, so that sufficient water- and oil-repelling properties can not be obtained. In addition, even if the film coating is sufficiently thick, its water- and oil-repelling properties are sometimes inadequate.

Furthermore, where a water-repelling oil-repelling film is provided on a transparent substrate such as a glass substrate, the transparency thereof is deteriorated due to the film thickness that is needed.

In addition, the surface and fluorine-based polymer coating are weakly coupled together for there are no chemical bonds between the two. Therefore, when the material is used for a substantially long time, the adhesion deteriorates resulting in a separation of the fluorine-based coating from the surface of the material.

Therefore, a material with a fluorine-based coating which is substantially free of pin holes, is uniform in thickness, and has excellent water- and oil-repelling properties is highly desirable.

SUMMARY OF THE INVENTION

The primary objective of this invention is to provide an adsorbed monomolecular film chemically bonded by a covalent bond each containing a —Si— group to the surface of a substrate either directly or via an inner layer, the adsorbed monomolecular film being constituted by at least two different molecules having different molecular lengths.

Another objective of this invention is to provide a process of manufacturing an adsorbed monomolecular film by a chemical adsorption process comprising the steps of:

preparing a coating composition which comprises a blend surface active material in a non-aqueous solvent, the blend surface active material comprising two groups of molecules differing in molecular chain length and having at one end a halosilane or alkoxysilane group; and contacting the coating composition with a substrate having at the surface thereof an active hydrogen capable of reacting with the halosilane or alkoxysilane, thereby forming a monomolecular film on the substrate surface.

Another objective of this invention is to provide a process of manufacturing an adsorbed monomolecular film by a chemical adsorption process comprising the steps of:

preparing a coating composition constituted by a surface active material in a non-aqueous solvent, the surface active material having at one end a halosilane or alkoxysilane group, and contacting the coating composition with a substrate having at the surface thereof an active hydrogen capable of reacting with the halosilane or alkoxysilane, thereby forming an inner layer on the substrate surface;

adding hydroxyl groups (—OH), amino groups (—NH$_2$), or imino groups (—NH) on the inner layer surface; and preparing a coating composition which comprises a blend surface active material in a non-aqueous solvent, the blend surface active material comprising two groups of molecules differing in molecular chain length and having at one end a halosilane or alkoxysilane group, and contacting the coating composition with an inner layer having at the surface thereof an active hydrogen capable of reacting with the halosilane or alkoxysilane, thereby laminating a monomolecular film on the inner layer surface.

It is preferable in this invention that at least two different molecules having different molecular lengths are alkyl fluoride groups.

It is preferable in this invention that the adsorbed monomolecular film is formed as a lamination on the inner layer and the inner layer has a substantially uniform thickness.

It is preferable in this invention that the inner layer is directly bonded by covalent bonds each having a —Si— group to the substrate surface and is also bonded by covalent bonds each having a —Si— group at the outer adsorbed monomolecular film.

It is preferable in this invention that the adsorbed monomolecular film has molecular surface irregularities.

It is preferable in this invention that the adsorbed monomolecular film is either water-repelling, oil-repelling, anti-fogging or anti-contaminating.

It is preferable in this invention that the adsorbed monomolecular film comprises at least two monomolecular compounds selected from the group consisting of formula [I] and [II]:

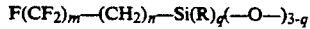

$$F(CF_2)_m-(CH_2)_n-Si(R)_q(-O-)_{3-q}$$

where m represents an integer ranging from 1 to 15, n represents an integer ranging from 0 to 15, the sum of m and n ranges from 10 to 30, q represents an integer ranging from 0 to 2, and R represents an alkyl group or an alkoxyl group.

$$F(CF_2)_s-(CH_2)_t-A-(CH_2)_p-Si(-R)_q(-O-)_{3-q}$$

where s represents an integer ranging from 1 to 8, t represents an integer ranging from 0 to 2, p represents an integer ranging from 5 to 25, q represents an integer ranging from 0 to 2, A represents a member of a group consisting of an oxy group (—O—), a carbonyl group (=CO), a carboxyl-ester group (—COO—) and dimethylsilylane group (—Si(CH$_3$)$_2$—), and R represents an alkyl group or an alkoxyl group.

It is preferable in this invention that the molecules of the blend surface active material have an alkyl fluoride group.

It is preferable in this invention that the molecules of the blend surface active material has at one end a trifluoromethyl group (—CF$_3$) and at the other end a chlorosilane group (—SiCl).

It is preferable in this invention that the blend surface active material contains at least two silane surface active materials represented by the formula selected from the group consisting of:

[III] F(CF$_2$)$_m$—(CH$_2$)$_n$—Si(—R)$_q$(—X)$_{3-q}$ where m represents an integer ranging from 1 to 15, n represents an integer ranging from 0 to 15, the sum of m and n ranges from 10 to 30 q represents an integer ranging from 0 to 2, represents an alkyl group or an alkoxyl group, and X represents a halogen atom or an alkoxyl group; and

[IV] F(CF$_2$)$_s$—(CH$_2$)$_p$—Si(—R)$_q$(—X)$_{3-q}$ where s represents an integer ranging from 1 to 8, t represents an integer ranging from 0 to 2, p represents an integer ranging from 5 to 25, q represents an integer ranging from 0 to 2, X represents a halogen atom or an alkoxyl group, R represents an alkyl group or an alkoxyl group, A represents a member of a group consisting of an oxy group (—O—), a carbonyl group (=CO), a carboxyl-ester group , (—COO—) and dimethylsilylane group (—Si(CH$_3$)$_2$).

DETAILED DESCRIPTION OF THE INVENTION

Figure 1:
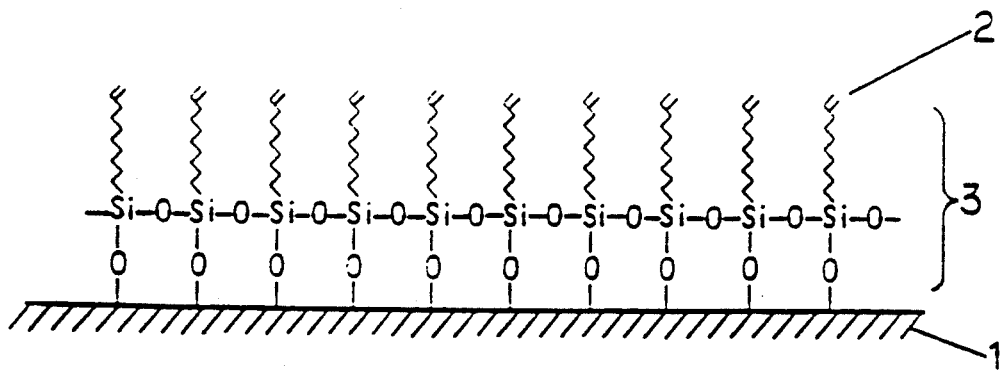
FIG. 1 is a schematic sectional view, enlarged in scale to the molecular level showing an inner layer having vinyl groups on the surface of a substrate as described in Example 1 of this invention.

According to the invention, the above problems are solved by a water-repelling, oil-repelling, anti-fogging, and anti-contaminating film comprising a monomolecular film formed on a substrate surface and containing alkyl fluoride groups, the monomolecular film having minimal surface irregularities wherein the irregularities are generally confined to the molecular level.

By incorporating onto the substrate surface a monomolecular film which contains a plurality of different fluorine groups having different molecular lengths, a coating in the form of a monomolecular film can be obtained which has minimal surface irregularities. Typically, such surface irregularities are confined to the molecular level. Because the surface has minimal irregularities and the molecules constituting the monomolecular film contain fluorine, the area of contact between water drops and the film surface can be reduced. Thus the film itself can have a very high water-repelling property. The film similarly repels oil drops, and therefore provides an improved oil-repelling property. With both of these effects, the anti-fogging and anti-contaminating properties can also be improved.

The substrate to be used according to the invention is of such materials as pure metals, e.g., aluminum, copper and iron, alloys or like composite materials, semiconductors, fiber, cloth, fabric, fur, leather, wood e.g., silicon and germanium, glass and plastics. According to the invention, a hydrophilic substrate is used. Where the substrate is made of a common base metal or a semiconductor, it is made hydrophilic by a natural oxide film formed on its surface. In case of a relatively non-hydrophilic substrate such as a plastic substrate, a hydrophilic property is imparted by, for instance, corona treatment, plasma treatment or an ion beam irradiation. Furthermore, with a relatively non-hydrophilic substrate, it is recommended to form a monomolecular film in advance of a surface active material having unsaturated carbon-carbon bond groups by using such means as a Langmuir-Blodgett's technique (hereinafter referred to a LB process) or a chemical adsorption process and then forcibly rendering the film hydrophilic by such means as causing breakage of the unsaturated bonds in an atmosphere containing oxygen, nitrogen, etc. This is preferred because many hydrophilic groups are formed on the surface of the substrate, and a high concentration of monomolecular film can be obtained at the surface of the substrate. As a reagent for rendering the substrate surface hydrophilic the following compounds may be used $CH_2=CH—(CH_2)_n—SiCl_3$ and $CH_2=CH—(CH_2)_n—COOH$ (where n represents an integer desirably about 10 to 20 ). The monomolecular film may be formed by ordinary means such as the LB process or the chemical adsorption process. Unsaturated bonds may be broken by ordinary means such as treatment with an electron beam, X-rays, gamma-rays, ultraviolet rays or an ion beam, plasma or corona treatment.

However, plastics having —NH groups such as polyamide or polyurethane substrates are not necessary in a surface oxygen treatment. Because —NH groups have active hydrogen, it is relatively easy to reduce the groups by initiating the dehydrochloric acid reaction using the chlorosilyl groups of the surface active agent.

The film coating according to the invention is formed by utilizing a very thin monomolecular film, and therefore the initial surface state of the substrate may be maintained as such.

The monomolecular film according to the invention may be formed on the substrate either directly or via a protective film or the like. Particularly, the monomolecular film according to the invention is suitably formed via such a functional film as a protective film, an anti-reflection film or an infrared-absorbing film. By doing so, it is possible to maintain high anti-reflecting or infrared-absorbing properties for a relatively long time and as well as to obtain a protective or like functional effect in addition to the water-repelling, oil-repelling, anti-fogging and anti-contaminating effects owing to the monomolecular film.

According to the invention, on a substrate surface is formed either directly or via a given film such as a protective film a water-repelling, oil-repelling, anti-fogging, and anti-contaminating film in the form of a monomolecular film, which contains a plurality of different kinds of fluorine (F) containing groups having different molecular lengths, the surface of which is predominantly confined to molecular irregularities. The monomolecular film may be formed by the LB process, the chemical adsorption process or any other usual process. In the chemical adsorption process, the reagent is adsorbed via chemical bonds to the substrate, and therefore this process is preferred to maintain highly close contact with the substrate. Moreover, high mechanical strength of the monomolecular film can be obtained.

Where the LB process is used to form the monomolecular film according to the invention, a carboxylic acid (—COOH) having an alkyl fluoride group in molecule a carboxylic acid salt, an ester, a trialcoxysilane, a trighydrosilane, etc. may be used.

Where the chemical adsorption process is used to form the monomolecular film according to the invention, fluorochlorosilane-based surface active materials containing an alkyl fluoride group and a chlorisilyl group, fluorotitanium-based surface active materials containing an alkyl fluoride group and a titanate group, fluorothiol surface active materials having an alkyl fluoride group and a thiol group may be used.

As for the fluorochlorosilane-based surface active agents to be used according to the invention, they are suitably those represented such as in the formulas [III] and [IV]. These fluorochlorosilane-based surface active materials are suitable because they are readily available and have pronounced water-repelling, oil-repelling, anti-fogging and anti-contaminating effects. They are suitably those represented by the formulas:

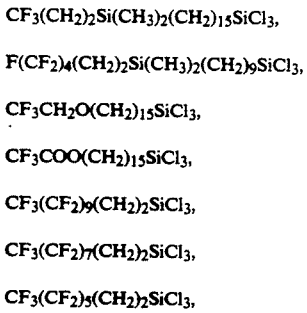

As the fluorotitanium-based or fluorothiol-based surface active agents for producing the monomolecular film according to the invention by the chemical adsorption process, those compounds obtained by substituting titanate or thiol for the chlorosilyl group of the above chlorosilane-based surface active material may be used.

Where an alkoxysilane-based surface active material is used, adsorption is effected with an alcohol removal reaction when forming a chemically adsorbed monomolecular film. When a fluorothiol-based surface active material is used, adsorption is effected with a hydrous reaction. These surface active materials are therefore preferred to surface active materials having chlorosilyl groups, because they do not cause damage to metal substrates.

The invention can widely be applied in the following uses. Materials made of metal, ceramic or plastic, glass, wood, stone, fiber, cloth, fabric, fur, leather, etc. are applicable to the substrate. The surface of the substrate can also be coated with paint or the like.

Examples of cutlery: a kitchen knife, scissors, a knife, a cutter, a graver, a razor, hair clippers, a saw, a plane, a chisel, a gimlet, a bodkin, bite (cutting tools), an edge of a drill, an edge of a mixer, a juicer, a blade of a mill, a blade of a lawn mower, a punch, a straw cutter, a staple of a stapler, a can opener or a surgical knife and the like.

Examples of needles: an acupuncture, a needle, a sewing needle, a matting needle, an injection needle, a surgical needle, a safety pin and the like.

Examples of products in pottery (ceramics) industry: products made of pottery, glass, ceramics or an enameled products. For example, sanitary potteries (a chamber pot, a wash-bowl, a bathtub, etc.), tableware (a rice-bowl teacup, a dish (plate) a bowl, a teacup, a glass, a bottle, a coffee-pot (siphon), a pan, an earthenware mortar (a cup and the like), vases (a flower bowl, a flowerpot, a bud vase and the like), water tanks (a breeding cistern, an aquarium water tank and the like), chemical experiment appliances (a beaker, a reactor vessel, a test tube, a flask, a laboratory dish, condenser, a mixing rod, a stirrer, a mortar, a bat, a syringe etc.) a roof tile, enameled ware, an enameled washbowl, an enameled pan and the like.

Examples of molding parts: dies for press molding, dies for case molding, dies for injection molding, dies for transfer molding, dies for compression molding, dies for transfer molding, dies for inflation molding, dies for vacuum molding, dies for blow forming, dies for extrusion molding, dies for fiber spinning, a calendar processing roll and the like.

Examples of forming molds for food: cake, cookies, bread-baking, chocolate, jelly, ice cream, an oven ware, an ice tray and the like.

Examples of cookware: kitchen utensils (a pan and a pot), a kettle, a pot, a frying-pan, a hot plate, a gridiron net, a takoyaki plate and the like.

Examples of resin(s): a polyolefin such as a polypropylene and polyethylene, a polyvinylchloride plastic, a polyamide, a polyimide, a polyamideimide, a polyester, an aromatic polyester, a polycarbonate, a polystyrene, a polysulfide, a polysulfone, a polyethersulfone, a polyphenylenesulfide, a phenolic resin, a furan resin, a urea resin, an epoxy resin, a polyurethane, a silicon resin, an ABS resin, a methacrylic resin, an acrylate resin, a polyacetal, a polyphenylene oxide, a polymethylpentene, a melamine resin, an alkyd resin, an unsaturated polyester cured resin and the like.

Examples of rubber(s): a styrene-butadiene rubber, a butyl rubber, a nitril rubber, a chloroprene rubber, a polyurethane rubber, a silicon rubber and the like.

Examples of household electric appliances: a refrigerator, a freezer, an air conditioner, a juicer, a mixer, a blade of an electric fan, a lighting apparatus, a dial plate, a dryer for a perm and the like.

Examples of sporting goods: skis, a fishing rod, a pole for the pole vault, a boat, a yacht, a surfboard, a fishing line, a float and the like.

Examples applying to vehicle parts:

(1) ABS resin: a lamp cover, an installment pannel, trimming parts, a protector for a motorcycle.

(2) Cellulose plastic: a car mark, a steering wheel (3) FRP (fiber reinforced plastics): a bumper, an engine cover (jacket)

(4) Phenolic resin: a brake (5) Polyacetal: wiper gear, a gas valve (6) Polyamide: a radiator fan (7) Polyacrylate (polycondensation polymerization by hisphenol A and pseudo phthalic acid): a direction indicator lamp (or lens) a cowl board lens, a relay case (8) Polybutylene terephthalate (PBT): a rear end, a front fender (9) Poly amino-bismaleimide: engine parts, a gear box, a wheel, a suspension drive system

(10) Methacrylate resin: a lamp cover lens, a meter pannel and its cover, a center mark

(11) Polypropylene: a bumper

(12) Polyphenylene oxide: a radiator grill, a wheel cap

(13) Polyurethane: a bumper, a fender, an installment pannel, a fan

(14) Unsaturated polyester resin: a body, a fuel tank, a heater housing, a meter pannel.

Examples of office supplies: a desk, a chair, a bookshelf, a rack, a telephone stand table, a rule (measure), a drawing instrument and the like.

Examples of building materials: materials for a roof, and outer wall and interiors. Roof materials such as brick, slate and tin (a galvanized iron sheet) and the like. Outer wall materials such as wood (including processed manufactured wood), mortar, concrete, ceramic sizing, metallic sizing, brick, stone, plastic and metal like an aluminum. Interior materials such as wood (including processed wood), metal like an aluminum, plastic, a paper, fiber and the like.

Examples of building stones: granite, marble and others for use as a building, a building material, an architecture, an ornament, a bath, a grave stone, a monument, a gatepost, a stone wall, a paving stone and the like.

Examples of the others: a high resisting voltage insulator such as a thermos bottle, a power supplying insulator for a vacuum system machinery or a spark plug, which has high water-repelling, oil-repelling, anti-fogging and anti-contaminating effects.

Specific examples of the process of chemical adsorption of a water-repelling, oil-repelling, anti-fogging, anti-contaminating film coating according to the invention will now be described with references to FIGS. 1 to 5.

EXAMPLE 1

A solution containing 80% wt n-hexadecane, 12% wt carbon tetrachloride and 8% wt chloroform was prepared by using $CH_2=CH-(CH_2)_{16}-SiCl_3$ as a silane surface active material and dissolving the same to a concentration of $3\times10^{-3}$ to $5\times10^{-2}$ mol, and a tempered glass substrate 1, as shown in FIG. 1, was held dipped in this solution at a room temperature for one hour. Since the surface of the substrate 1 contained hydroxyl groups, a reaction between the chlorosilyl groups of the chlorosilane-based surface active material and the hydroxyl groups, thus forming on the surface bonds represented such as the formula [1].

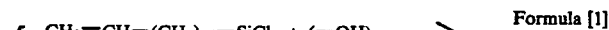
Formula [1]

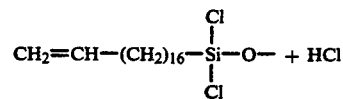

The tempered glass substrate 1 was then washed by FREON113 ®, $CCl_2F-CC_2F_2$, to remove the material remaining on the surface without reaction, followed by washing with water or exposing to air to react with moisture in the air. The —SiCl group was changed to a —SiOH groups as in formula [2].

Formula [2]

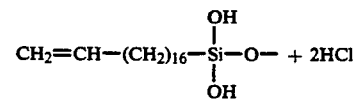

Each silanol group (—SiOH) was then dehydrated and crosslinked to form a siloxane bond (—SiO) as in formula [3].

Formula [3]

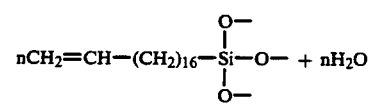

By the consecutive reaction, a single adsorbed monomolecular film 3 having vinyl ($CH_2=CH-$) groups 2 was formed to a thickness of about 2.5 nm such that it was chemically bonded (covalent bond) to a protective film via oxygen atoms.

Figure 2:
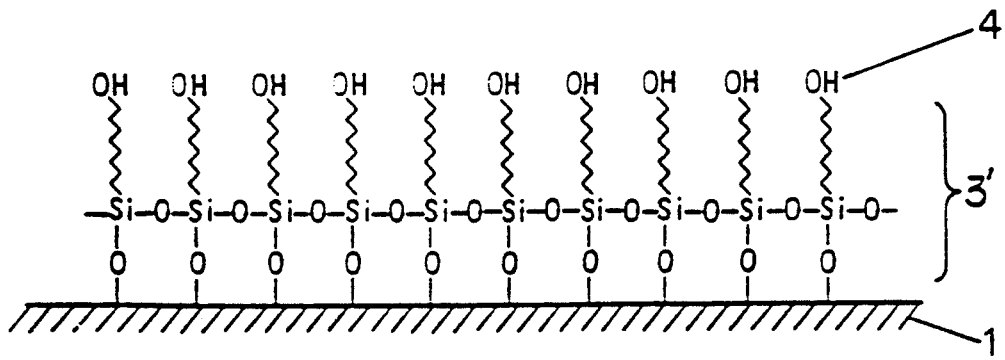
FIG. 2 is a schematic sectional view, enlarged in scale to the molecular level showing the inner layer forming hydroxy groups on the surface of a substrate as described in Example 1 of this invention.
Figure 3:
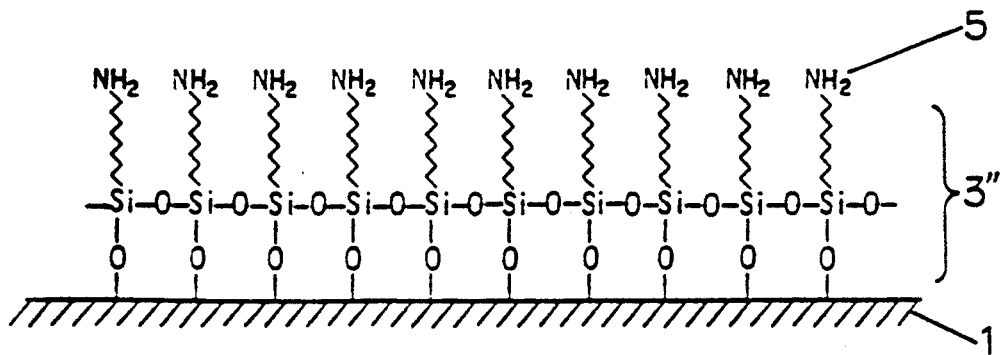
FIG. 3 is a schematic sectional view, enlarged in scale to the molecular level showing the inner layer forming amino groups on the surface of a substrate as described in Example 1 of this invention.

This glass substrate 1 was irradiated with about 3 Mrad. of X-rays in an atmosphere containing oxygen and also in an atmosphere containing nitrogen. Where the substrate 1 was irradiated in the oxygen-containing atmosphere, a monomolecular film 3' (inner layer), as shown in FIG. 2, was obtained, which contained hydroxyl (—OH) groups 4 added to the vinyl groups 2. Where the irradiation was done in the nitrogen-containing atmosphere, a monomolecular film 3" (inner layer) was obtained, as shown in FIG. 3, which contained amino groups (—NH$_2$) 5 added to the vinyl groups 2. The addition of the functional groups, i.e., the —OH, —NH$_2$ and —NH groups, to the vinyl groups, was confirmed as a result of a FTIR analysis.

Subsequent to the addition of —OH groups, a solution containing 80% wt n-hexadecane, 12% wt carbon tetrachloride and 8% wt chloroform was prepared by using

as respective chemical adsorption reagents and dissolving these reagents to respective concentrations of about $2 \times 10^{-3}$ to $5 \times 10^{-2}$ Mol and at a mixing ratio of 3:1 to 1:3, and the glass substrate 1 forming the monomolecular film 3', as shown in FIG. 2, was dipped into the solution and held for one hour. Since —OH groups 4 were exposed at the surface of the substrate 1, the chlorosilic groups of the chlorosilane- based surface active material having fluorine and —OH groups 4 were reacted. Thus, bonds represented by formulas [4] and [5] were produced on the surface substantially at the above mixing ratio. This reaction proceeded substantially the same as above in formulas [1] to [3].

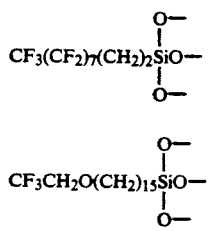

Formula [4]

Formula [5]

Figure 4:
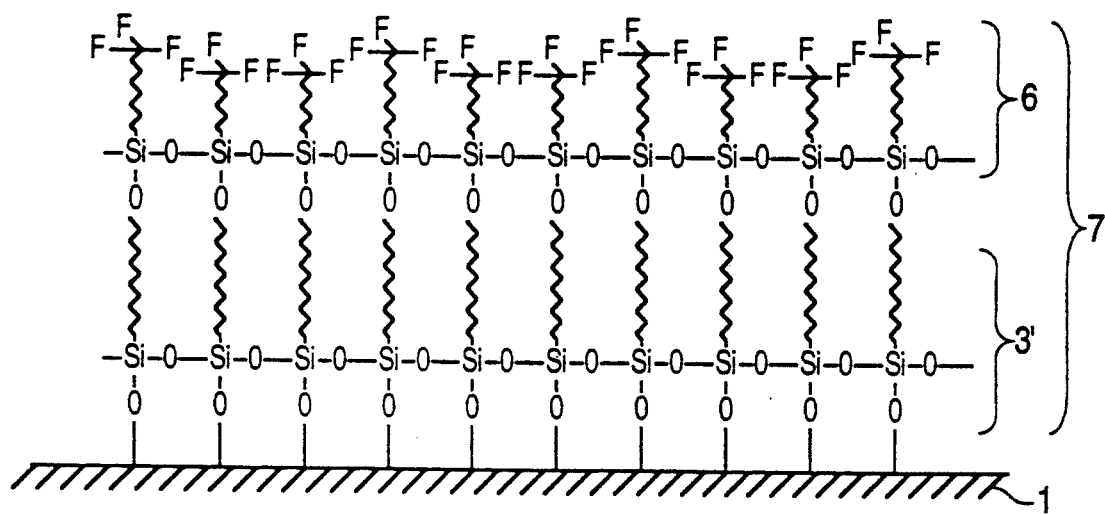
FIG. 4 is a schematic sectional view, enlarged in scale to the molecular level showing the laminating monomolecular film on the inner layer surface of a substrate as described in Example 1 of this invention.

Thus, a high concentration monomolecular lamination film 7 can be obtained on the surface of the glass substrate 1, as shown in FIG. 4. The film 7 includes an adsorbed monomolecular film 6 which has a fluorine group and surface irregularities which are generally molecular surface irregularities. The adsorbed monomolecular film is chemically bonded (i.e., covalently bonded) to the inner layer 3'.

The wetting angle to water, measured at the surface of the adsorbed monomolecular film 6, was from 140 to 150 degrees. The measured value showed an improvement by about 20 to 30 degrees from 120 degrees, which was obtained by using only a single kind of fluorosilane-based surface active material. The resultant glass therefore can be used to obtained a wiper-free vehicle window glass and to prevent fogging on, for instance, glass lens surfaces.

Figure 5:
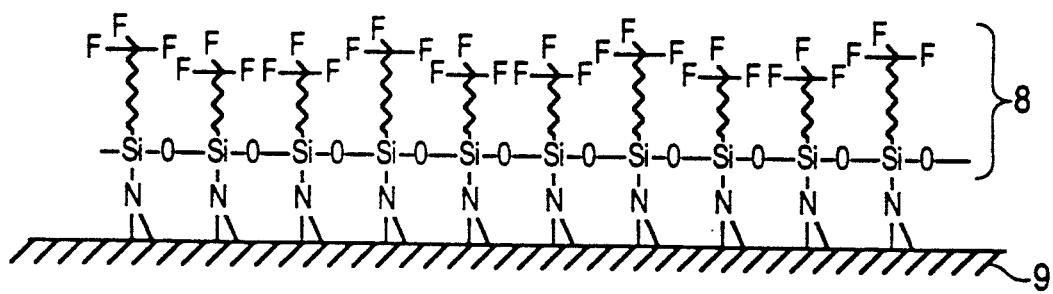
FIG. 5 is a schematic sectional view, enlarged in scale to the molecular level showing the monomolecular film on the surface of a Nylon-6,6 substrate as described in Example 2 of this invention.

These effects can be obtained by forming a monomolecular film containing alkyl fluoride groups on the outermost substrate surface wherein the alkyl fluoride groups have different molecular lengths such as formulas 4 and 5, with the surface being substantially pin hole free.

Where no intermediate monomolecular film is necessary between the surface water-repelling, oil-repelling film and the glass substrate, a singularly adsorbed monomolecular film 8 containing fluorine may be formed on a glass surface, as shown in FIG. 5, by using a chlorosilane-based surface active material having fluorine and a mixing ratio of, for example, 1:1. Such a glass was shown to have sufficient water- and oil-repelling properties.

Where a plurality of intermediate monomolecular films are necessary, the steps of chemical adsorption and subsequent radiation irradiation are repeated a number of times corresponding to the necessary laminated film number. For example, $CH_2=CH(CH_2)_{16}$—$SiCl_3$ and a plurality of different chlorosilane-based surface active materials having a fluorine group and different molecular lengths can be adsorbed as adsorption reagents. By doing so, a water-repelling, oil-repelling film having a single fluorine-containing adsorbed monomolecular film can be formed on a glass surface via a number of intermediate laminated monomolecular films.

In the above example, as the reagent for forming the outermost surface adsorbed monomolecular film containing fluorine and dimethylsilane or an oxygen atom or a carboxy ester the following can be used:

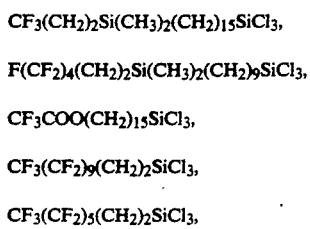

EXAMPLE 2

A solution containing 80% wt n-hexadecane, 12% wt carbon tetrachloride and 8% wt chloroform was prepared by using $CF_3(CF_2)_7(CF_2)_2SiCl_3$ and $CF_3CH_2O(CH_2)_{15}SiCl_3$ as silane surface active materials. The surface active materials were each dissolved to a concentration of 1% wt. A Nylon-6,6 substrate was dipped into this solution and held at room temperature for one hour. Since the surface of the Nylon-6,6 substrate contained imino groups (—NH), a reaction between the chlorosilyl groups of the chlorosilane-based surface active material and the imino groups formed surface bonds as represented in the formulas [6] and [7]. This reaction proceeded substantially as in formulas [1] to [3].

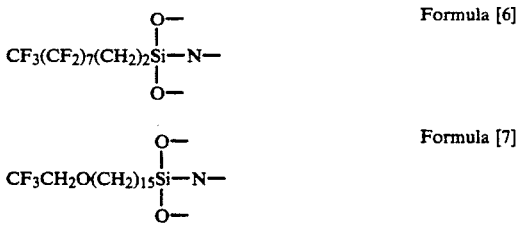

Formula [6]

Formula [7]

Thus, a high concentration monomolecular film 8 can be obtained on the surface of the Nylon-6,6 substrate 9 as shown in FIG. 5. The adsorbed monomolecular film 8 has a fluorine group and surface irregularities which are generally molecular surface irregularities. The adsorbed monomolecular film is chemically bonded (i.e., covalently bonded) to the substrate 9.

The wetting angle to water, measured at the surface of the monomolecular adsorbed film 8, was from 140 to 150 degrees. A water-repelling, oil-repelling film having a single fluorine-containing monomolecular adsorbed film was formed on the substrate 9.

EXAMPLE 3

This example, like Example 1, concerns the formation of the water-repelling, oil-repelling, anti-fogging, anti-contaminating film coating by the LB process using a tempered glass substrate.

A blend surface active agent was obtained by mixing two different surface active materials, i.e., $CF_3(CF_2)_7(CH_2)_2COOH$ and $CF_3CH_2O(CH_2)_{15}COOH$, at a mixing ratio of 1:1, and 10 mg was dissolved in 100 g of chloroform. The solution was then developed on the water surface.

A tempered glass substrate as in Example 1 was then dipped at a speed of 1 cm/min. under a pressure of 50 mN/m and then raised.

As a result, a film coating having molecular surface irregularities and containing alkyl fluoride groups was formed on the tempered glass substrate. This film coating had the same water-repelling property as the film obtained in Example 1.

The water-repelling effect obtained in this example is attributable to the fact that like Example 1 the monomolecular film containing alkyl fluoride groups is formed as the outermost surface layer on the substrate. The alkyl fluoride groups are characterized by having different constituent molecules different molecular lengths and are substantially pin hole free.

Any of the above examples can also use two different surface active materials in combination. By using three or more different reagents, a monomolecular film having three or more different reagents can be obtained. Such a monomolecular film has similar water- and oil-repelling effects.

Where a glass surface has a protective film or anti-reflecting film such as metal or a metal oxide film, or an infrared-absorbing film such as color formed infrared film, a chemically adsorbed film can be formed by appropriately controlling the adsorption time so long as the surface has hydrophilic groups such as hydroxyl groups.

Adsorbed films can also be obtained under similar conditions by using, in lieu of the above chlorosilane-based surface active materials, fluorotitanate-based surface active materials such as a combination of $F(CF_2)_8Si(CH_3)_2(CH_2)_9TiOCH(CH_3)_2$ and $CF_3(CF_2)_9(CH_2)_2TiOCH(CH_3)_2$, or $F(CF_2)_4(CH_2)_2Si(CH_3)_2(CH_2)_9TiCl_3$, $CF_3(CF_2)_5(CH_2)_2SiTi_3$, or a fluorothiol-based surface active material such as a combination of $F(CF_2)_4(CH_2)_{20}(CH_2)_{15}SH$ and $CF_3(CF_2)_9(CH_2)_2SH$ or adsorption liquids which can be obtained by adding, for instance, $CH_3(CH_2)_{19}SH$ to chlorosilane-based or fluorotitanate-based or fluorothiol-based surface active agents.

While the above examples, are primarily concerned with tempered glass substrates, the invention is applicable to all kinds of glass, which require improved water- and oil-repelling properties such as window glass or mirrors used for buildings or vehicles, trains and airplanes or glass vessels or lenses.

With a glass substrate having surface irregularities on the order of microns, the anti-contaminating property is slightly inferior. However, the water wetting angle is from 145 to 155 degrees, and the water- and oil-repelling properties and anti-fogging property are improved.

The water-repelling, oil-repelling, anti-fogging, anti-contaminating film coating according to the invention can be formed not only on glass substrates, but the invention is applicable to substrates made of metals semiconductors, plastics, etc. as well.

As has been described in the foregoing, the water-repelling, oil-repelling, anti-fogging, anti-contaminating film coating according to the invention comprises a monomolecular film formed on a substrate surface and having minimal surface irregularities which are generally confined to irregularities at the molecular level. Thus, it is possible to form a high density organic thin film coating, which is substantially free of pin holes, has a uniform thickness, is very thin and has excellent water- and oil-repelling properties. That is, with the treatment according to the invention, it is possible to obtain a highly durable surface treatment and prevent contamination, fogging and wetting of substrate surfaces.

As has been shown, the invention is greatly beneficial to industry.

The invention may be embodied in other specific forms without departing from the spirit or essential characteristics thereof. The present embodiment is to be considered in all respects as illustrative and not restrictive, the scope of the invention being indicated by the appended claims rather than by the foregoing description and all changes which come within the meaning and range of equivalency of the claims are intended to be embraced therein.

What is claimed is:

1. A process of manufacturing an adsorbed monomolecular film by a chemical adsorption process comprising the steps of:

preparing a coating composition comprising a blend surface active material in a non-aqueous solvent, the blend surface active material comprising at least two different groups of molecules different in molecular chain length and having at one end a halosilane or alkoxysilane group; and contacting said coating composition with a substrate having at the surface thereof an active hydrogen capable of reacting with said halosilane or alkoxysilane group, allowing said active hydrogen to react with said halosilane or alkoxysilane group, thereby forming a monomolecular film on the substrate surface.

2. The method of manufacturing an adsorbed monomolecular film according to claim 1, wherein each molecule of the blend surface active material comprises an alkyl fluoride group.

3. The method of manufacturing an adsorbed monomolecular film according to claim 2, wherein each molecule of the blend surface active material has at one end a trifluoromethyl group (—CF$_3$) and at another end a chlorosilane group (—SiCl).

4. The method of manufacturing an adsorbed monomolecular film according to claim 1, wherein said blend surface active material comprises a silane surface active material which is represented by the formula:

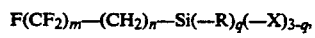

where m represents an integer ranging from 1 to 15, n represents an integer ranging from 0 to 15, the sum of m and n ranges from 10 to 30, q represents an integer ranging from 0 to 2, R represents an alkyl group or alkoxyl group, and X represents a halogen atom or an a group;

or is represented by the formula:

where s represents an integer from 1 to 8, t represents an integer ranging from 0 to 2, p represents an integer ranging from 5 to 25, q represents an integer ranging from 0 to 2, R represents an alkyl or an alkoxyl group, X represents a halogen atom or an alkoxyl group, and A is a group selected from the group consisting of an oxy group (—O—), a carbonyl group (=CO), a carboxylester group (—COO—) and a dimethylsilylane group (—Si(CH$_2$)$_2$—).

5. A process of manufacturing an adsorbed monomolecular film by a chemical adsorption process comprising the steps of:

preparing a coating composition comprising a surface active material in a non-aqueous solvent, the surface active material having at one end a halosilane or alkoxysilane group, contacting said coating composition with a substrate having at the surface thereof an active hydrogen capable of reacting with said halosilane or alkoxysilane group, allowing said active hydrogen to react with said halosilane or alkoxysilane group, thereby forming an inner layer on the substrate surface;

adding hydroxyl groups (—OH), amino groups (—NH$_2$), or imino groups (—NH) on said inner layer surface;

preparing a coating composition comprising a blend surface active material in a non-aqueous solvent, the blend surface active material comprising at least two different groups of molecules different in molecular chain length and having at one end a halosilane or alkoxysilane group, and contacting said coating composition with an inner layer having at the surface thereof an active hydrogen capable of reacting with said halosilane or alkoxysilane group, thereby laminating a monomolecular film onto said inner layer surface.

* * * * *